(12) United States Patent
Dvonch

(10) Patent No.: US 9,995,677 B2
(45) Date of Patent: Jun. 12, 2018

(54) SILICON ARTICLE INSPECTION SYSTEMS AND METHODS

(71) Applicant: Sensors Unlimited, Inc., Princeton, NJ (US)

(72) Inventor: Curt Dvonch, Pennington, NJ (US)

(73) Assignee: Sensors Unlimited, Inc., Princeton, NJ (US)

(*) Notice: Subject to any disclaimer, the term of this patent is extended or adjusted under 35 U.S.C. 154(b) by 0 days. days.

(21) Appl. No.: 15/257,621

(22) Filed: Sep. 6, 2016

(65) Prior Publication Data

US 2018/0067042 A1    Mar. 8, 2018

(51) Int. Cl.
*G01J 5/02* (2006.01)
*G01N 21/3563* (2014.01)
*G01N 21/95* (2006.01)

(52) U.S. Cl.
CPC ..... *G01N 21/3563* (2013.01); *G01N 21/9505* (2013.01); *G01N 2021/3568* (2013.01)

(58) Field of Classification Search
CPC ................. G01N 23/3563; G01N 21/9505
USPC ........................................ 250/340
See application file for complete search history.

(56) References Cited

U.S. PATENT DOCUMENTS

| 6,593,156 B2 | 7/2003 | Nikawa |
| 6,753,524 B2 | 6/2004 | Matsui et al. |
| 7,729,528 B2* | 6/2010 | O'Dell ...................... 250/559.39 |
| 9,165,844 B2 | 10/2015 | Fulle et al. |
| 9,255,894 B2 | 2/2016 | VanHoomissen et al. |
| 9,355,919 B2 | 5/2016 | Estermann et al. |
| 2015/0069247 A1* | 3/2015 | Asundi .................. G01N 21/23 250/341.3 |

* cited by examiner

*Primary Examiner* — David Porta
*Assistant Examiner* — Meenakshi Sahu
(74) *Attorney, Agent, or Firm* — Locke Lord LLP; Scott D. Wofsy; Christopher J. Cillié

(57) ABSTRACT

A method of inspecting a silicon article includes irradiating a silicon article with infrared radiation, transmitting a portion of the infrared radiation through the silicon article, and filtering the infrared radiation transmitted through the silicon article. Image data is acquired from the filtered infrared radiation and an image of the silicon article reconstructed from the image data. Based on the reconstructed image of the silicon article, one or more anomalies defined within the silicon article are identified.

17 Claims, 4 Drawing Sheets

SILICON ARTICLE INSPECTION SYSTEMS AND METHODS

BACKGROUND OF THE INVENTION

1. Field of the Invention

The present disclosure relates to silicon structures, and more particularly to detecting anomalies within silicon structures.

2. Description of Related Art

Microelectronics and micromechanical devices, such as integrated circuits, sensors and actuators, commonly include structures formed on a silicon substrate. The structures are generally formed by operations that selectively add and remove material from the silicon substrate, such as patterning, etching, and/or deposition. The silicon substrate is typically fixed within the device such that functionality provided by the structures is available to the device.

Some silicon substrate and bonds can include internal voids, surface connected cracks, and internal cracks. Since devices can have different sensitivities to internal voids, surface connected cracks, and/or internal cracks in substrates and bonds, the density and disposition of such anomalies within a given silicon substrate or bond can be of interest for purposes of characterizing the suitability of given silicon substrate to the processes necessary to fabricate a contemplated structure and/or assessing the reliability of a device incorporating the bond. For that reason techniques like optical inspection and scanning acoustic microscopy (SAM) techniques are used to identify anomalies within silicon substrate and bonds. Certain types of anomalies are readily discernable with optical inspection. Other types of anomalies require SAM inspection techniques to supplement the optical inspection to characterize the substrate or bond.

Such conventional methods and systems have generally been considered satisfactory for their intended purpose. However, there is still a need in the art for improved systems and method for inspecting silicon wafers. The present disclosure provides a solution for this need.

SUMMARY OF THE INVENTION

A method of inspecting a silicon article includes irradiating a silicon article with infrared radiation, transmitting a portion of the infrared radiation through the silicon article, and filtering the infrared radiation transmitted through the silicon article. Image data is acquired from the filtered infrared radiation and an image of the silicon article reconstructed from the image data. Based on the reconstructed image of the silicon article, one or more anomalies defined within the silicon article are identified.

In certain embodiments, the silicon article can include a silicon wafer. The silicon article can include a bond connecting a first silicon article to a second silicon article. Irradiating the silicon article can include irradiating an entirety of a surface of the silicon article using a halogen lamp. Irradiating the silicon article can include irradiating the silicon wafer with broadband radiation, such as with broadband radiation from a halogen lamp.

In accordance with certain embodiments, the broadband radiation can include visible radiation. The broadband radiation can include infrared radiation. The broadband radiation can include narrowband centered at 1200 nanometers. The narrowband radiation can have a bandwidth that is about 20 nanometers or smaller. It is contemplated the method can include distinguishing between a void, a surface connected crack, and an internal crack defined with the silicon article.

It is also contemplated that, in accordance with certain embodiments, acquiring image data can include receiving the filtered radiation at a broadband sensor array. Acquiring image data can include measuring the filtered radiation within a wavelength band extending between about 800 nanometers and about 1700 nanometers. Reconstructing an image of the silicon article can include reconstructing an image including a notch of a silicon wafer. Identifying the one or more anomalies defined within the silicon article can include identifying one or more of a void, a surface connected crack, and an internal crack defined within the silicon article.

A silicon article inspection apparatus includes an illuminator, a sensor array, a manipulator, and filter. The illuminator is arranged to illuminate a silicon article with broadband radiation. The sensor array is optically coupled to the illuminator and is arranged to generate image data from radiation emitted by the illuminator and transmitted by the silicon article. The manipulator is arranged to insert and remove the silicon article from an inspection position defined between the illuminator and the sensor array. The filter is disposed between the inspection location and the sensor array and transmits narrowband radiation centered at 1200 nanometers.

In certain embodiments, the illuminator can include a halogen lamp. The silicon article can have one or more of a surface connected crack, an internal crack, and a void defined with a bulk silicon layer and a bond between a first silicon layer and a second silicon layer. The sensor array can have a high responsivity within a wavelength band between 900 nanometers and 1700 nanometers. The filter can be opaque to incident radiation outside of a narrowband between 1190 nanometers and 1210 nanometers.

A silicon article inspection system can include a silicon article inspection apparatus as described above and a control module. The control module is be operatively connected to the silicon article inspection apparatus is responsive to instructions recorded on a non-transitory machine-readable medium to perform the above described method.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
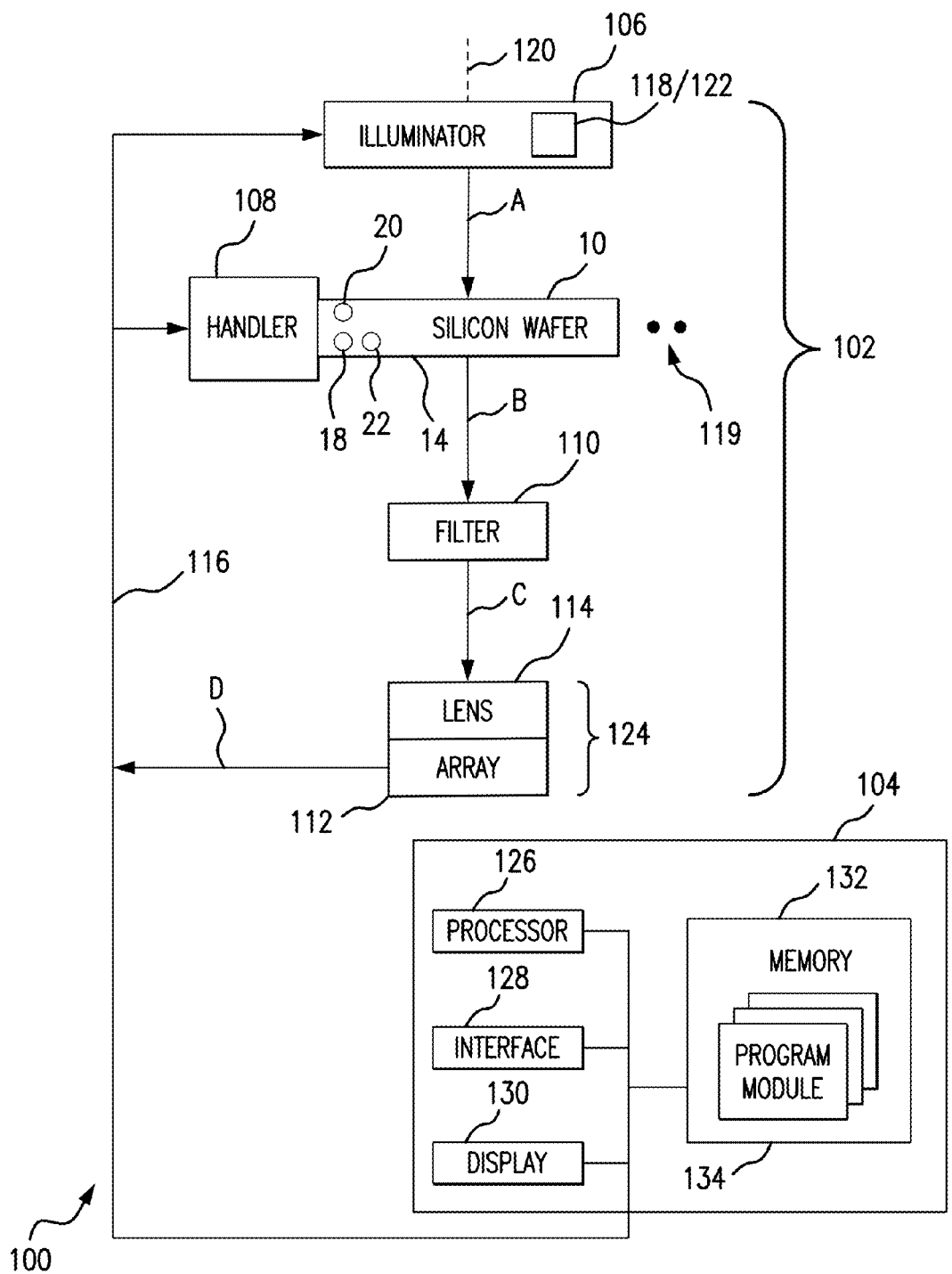
FIG. 1 is a schematic diagram of an exemplary embodiment of a wafer inspection system constructed in accordance with the present disclosure, showing a silicon wafer transmitting radiation received from an illuminator to a narrowband filter.

Reference will now be made to the drawings wherein like reference numerals identify similar structural features or aspects of the subject disclosure. For purposes of explanation and illustration, and not limitation, a partial view of an exemplary embodiment of a silicon article inspection system in accordance with the disclosure is shown in FIG. 1 and is designated generally by reference character 100. Other embodiments of silicon article inspection systems, apparatus, and methods of inspecting silicon articles in accordance with the disclosure, or aspects thereof, are provided in FIGS. 2-4, as will be described. The systems and methods described herein can be used inspecting silicon articles such as silicon wafers for anomalies like cracks and internal voids.

Referring to FIG. 1, a silicon article inspection system 100 is shown. Silicon article inspection system 100 includes a silicon article inspection apparatus 102 and a control module 104. Silicon article inspection apparatus 102 includes an illuminator 106, an article handler 108, a filter 110, and an array 112. Silicon article inspection apparatus 102 also includes an infrared lens 114 and a link 116. Control module 104 is operatively connected to silicon article inspection apparatus 102, and in the illustrated exemplary embodiment is operatively connected to illuminator 106, article handler 108, and array 112 through link 116.

Illuminator 106 has a radiation source 118. Radiation source 118 includes a broadband radiation source for illuminating a silicon wafer 10. Radiation source 118 is a broadband radiation source that, in the illustrated exemplary embodiment generates radiation in both the visible portion of the electromagnetic spectrum and the infrared portion of the electromagnetic spectrum. It is contemplated that radiation source 118 can include a halogen bulb. The halogen bulb can be arranged to illuminate substantially the entire surface 12 of silicon wafer 10. As will be appreciated by those of skill in the art in view of the present disclosure, illuminating substantially the entire surface of silicon wafer 10 with silicon wafer 10 fixed relative to radiation source 118 improves throughput by eliminating the need to move either (or both) illuminator 106 relative to silicon wafer 10 during inspection. As will also be appreciated by those of skill in the art in view of the present disclosure, halogen lamps are relatively inexpensive, rendering silicon inspection system 100 relatively inexpensive to operate.

In certain embodiments, illuminator 106 can include a narrowband radiation source 122. Narrowband radiation source 122 has the advantage of creating a relatively low power, lower operating temperature system. This potentially removes the need for filter 110, reducing complexity and/or cost of the system 100.

Wafer hander 108 is arranged to position silicon wafer 10 between illuminator 106 and array 112 at an inspection position 119. It is contemplated that wafer handler 108 be arranged to adjust the position of silicon wafer 10 along an optical axis 120 extending between illuminator 106 and array 112. In this respect wafer handler can be configured to position silicon wafer 10 such that substantially the entire surface of silicon wafer 10 is illuminated by illuminator 106.

Array 112 includes a photodiode array responsive to infrared radiation received along optical axis 120. The photodiode array generates image data D using infrared radiation emitted by illuminator 106 and transmitted by silicon wafer 10 from illuminator 106 along optical axis 120. As the infrared radiation is transmitted by silicon wafer 10 the transmitted radiation is modulated by silicon wafer 10 to include information relating to anomalies disposed within silicon wafer 10, e.g., internal voids 18, surface connected cracks 20, and internal cracks 22.

Array 112 is optically connected to a lens 114 along optical axis 120 and is arranged axially on a side of lens 114 opposite inspection position 119. Lens 114 may be arranged to collect infrared radiation traversing optical axis 120 and matches the aperture of array 112 with the transmitting area of lower surface 14 of silicon wafer 10. This enables silicon article inspection system 100 to acquire image data of silicon wafers of different sizes, e.g., 4 inch, 6 inch, 8 inch, or 12 inch wafers. It is contemplated that array 112 be responsive to infrared radiation having wavelengths between 900 nanometers and 1700 nanometers. Examples of suitable camera arrangements include compact large format InGaAs cameras, such as the SU640KTS-1.7RT model infrared camera, available from Sensors Unlimited Inc. of Princeton, N.J., a United Technologies Aerospace Systems Company.

Existing techniques of silicon wafer defect detection, such as scanning acoustic microscopy (SAM) inspection, near infrared (NIR) imaging, and wideband shortwave infrared (SWIR) imaging, impose limitations on the inspection process. SAM inspection is typically able to comprehensively identify defects in silicon wafers, but is unable to differentiate between anomaly types, is slow, and is relatively expensive in comparison to imaging. NIR imaging and wideband SWIR imaging are relatively fast in comparison to SAM inspection, but may be unable to detect all anomaly types.

Using a discrete wavelength inspection methodology, Applicant has determined that infrared radiation within a narrowband around 1200 nanometers enables low cost, high speed quantification of internal anomalies within silicon wafers as well as classification of anomalies according to anomaly type. In this respect, without being bound by a specific model or mechanism, it is believed that the absorptivity of silicon oxide bounding internal voids varies from the native silicon bounding a surface connected or internal crack that, at wavelengths around 1200 nanometers, internal voids are distinguishable in imagery acquired using infrared radiation transmitted by the silicon wafer. This enables grading silicon wafers according to anomaly type and well as total anomalies without requiring the use of scanning atomic microscopy (SAM) technique. As will be appreciated by those of skill in the art, this simplifies the process of grading silicon wafers, for example, during silicon wafer recycling.

Filter 110 is configured to transmit radiation having wavelength in a narrowband including 1200 nanometers and is arranged between illuminator 106 and array 112 along optical axis 120. Filter 110 transmits infrared radiation having a narrowband centered around 1200 nanometers. In accordance with certain embodiments, the narrowband extends between 1190 nanometers and 1210 nanometers, eliminating the need for filter 110. It is also contemplated that the transmitted infrared radiation can have a wavelength on only 1200 nanometers. Filtering the transmitted radiation to a narrowband including 1200 nanometers reduces the signal to noise ratio in infrared radiation received by array 112. Notably, since the information enabling classification of defects appears to reside within a finite bandwidth including 1200 nanometers, filtering the infrared radiation to within the range of 1190 nanometers to 1210 nanometers improves the signal to noise ratio of information relating to anomalies received at array 112.

Control module 104 includes a processor 126. Processor 126 is communicative with an interface 128, a display 130 and a memory 132. Memory 132 includes a non-transitory machine-readable medium having recorded on it a plurality of program modules 134. Program modules 134 include instructions recorded thereon that, when read by processor 126, cause processor 126 to undertake certain actions. Among those actions are embodiments of methods inspecting silicon articles, such as silicon wafer 10 and/or a silicon article 30 (shown in FIG. 2). It is to be understood and appreciated that control module 104 can be implemented as software, circuitry, or as both software and circuitry.

For example, in contemplated embodiments, control module 104 causes illuminator 106 to emit broadband radiation A including visible and infrared wavelengths along optical axis 120. Silicon wafer 10 receives broadband radiation A and transmits attenuated radiation B along optical axial 120. It is contemplated that attenuated radiation B include infrared radiation, and in certain embodiments includes substantially no radiation having visible wavelengths.

Filter 110 receives attenuated radiation B along optical axis 120, narrowband filters attenuated radiation B, and transmits narrowband radiation C along optical axis 120. Narrowband radiation C has a bandwidth centered at 1200 nanometers. In certain embodiments narrowband radiation C has a bandwidth extending between 1190 nanometers and 1210 nanometers. In accordance with certain embodiments, narrowband radiation C is limited to radiation having a wavelength of only 1200 nanometers. Narrowband radiation C includes information relating to voids and/or cracks within silicon wafer 10, which array 112 provides to control module 104 as image data D. Control module 104 reconstructs an image E (shown in FIG. 4A) of silicon wafer 10 using image data D, image E indicating locations of internal voids 18, surface connected cracks 20, and internal cracks 22 defined within silicon wafer 10.

Figure 2:
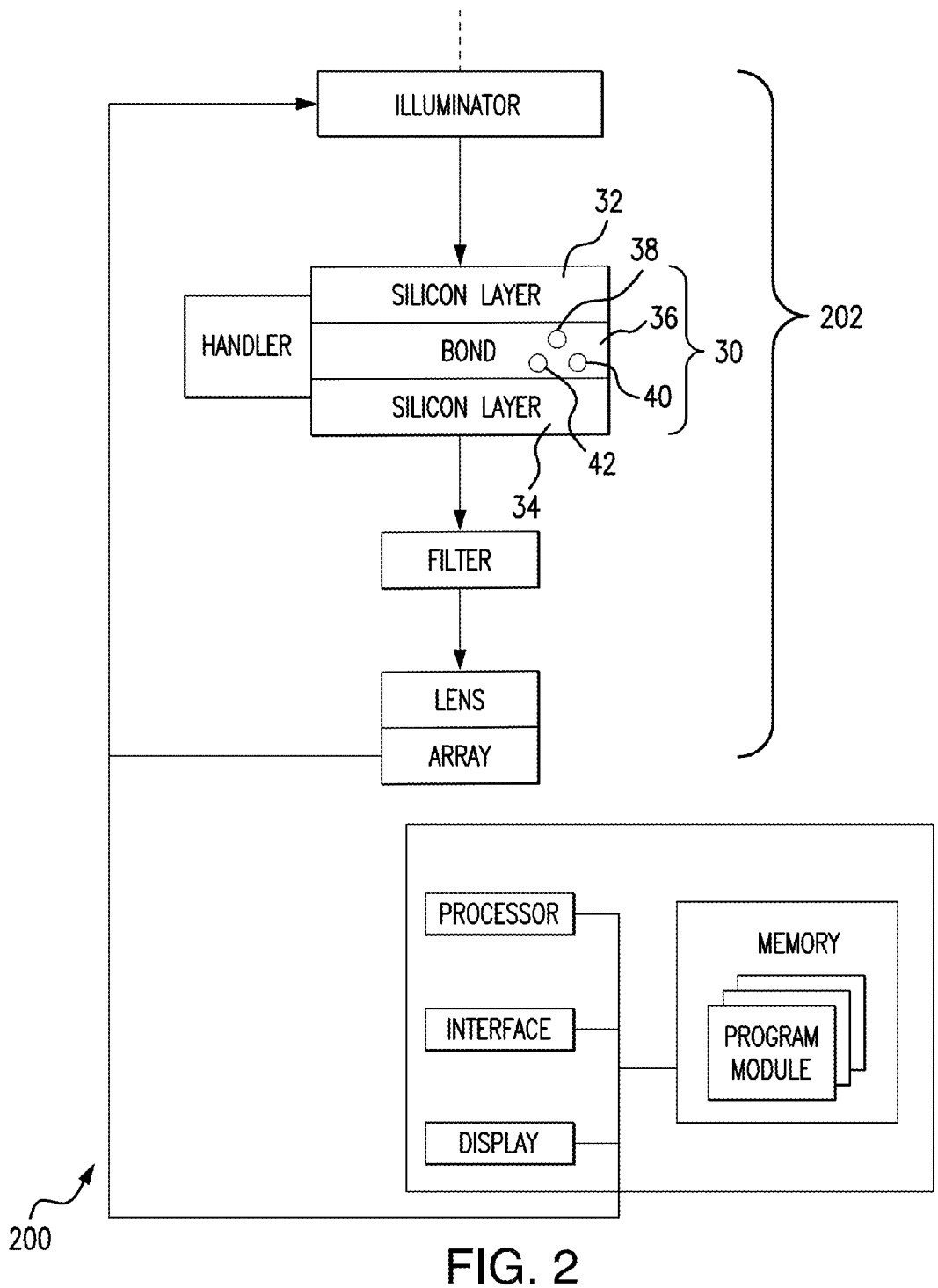
FIG. 2 is a schematic diagram of another exemplary embodiment of a wafer inspection diagram constructed in accordance with the present disclosure, showing a silicon article transmitting radiation received from an illuminator to a narrowband filter.

With reference to FIG. 2, a silicon article inspection system 200 is shown. Silicon article inspection system 200 is similar to silicon article inspection system 100 and additionally includes a silicon inspection apparatus 202 with a silicon article handler 208. Silicon article handler 208 is arranged for positioning a silicon article 30 having a first silicon layer 32 coupled to a second silicon layer 34 by a bond 36. Bond 36 includes one or more of an internal void 38, a surface connected crack 40, and an internal crack 42. Internal void 38, surface connected crack 40, and internal crack 42 are discernable in image data generated by array 212 for generating imagery suitable for inspecting bond 36.

Figure 3:
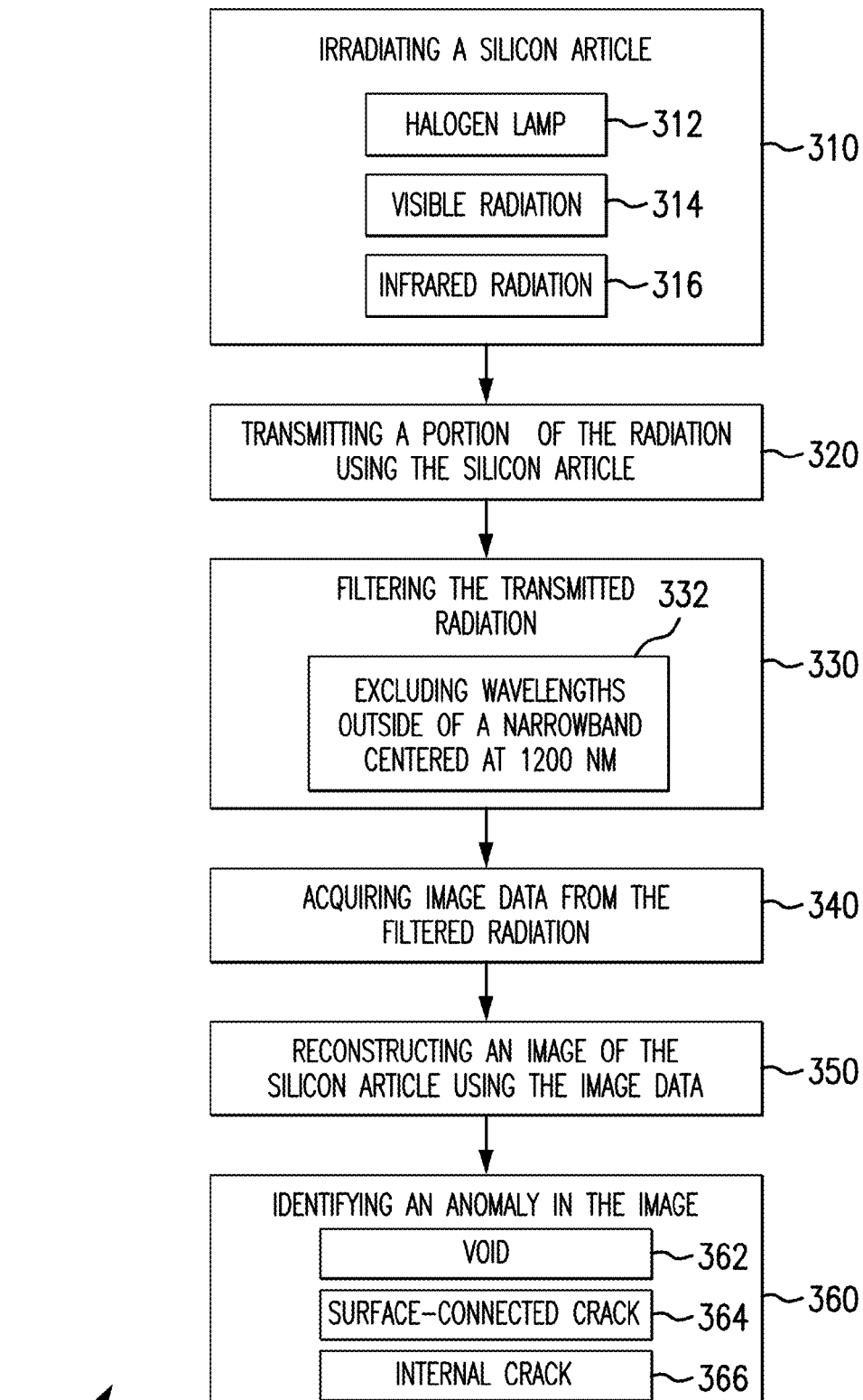
FIG. 3 is a block diagram of a method of inspecting a silicon article, showing operations for generating image data using radiation received from a filter at a sensor array.

With reference to FIG. 3, a method 300 of inspecting a silicon article, e.g., silicon wafer 10 (shown in FIG. 2) or silicon article 30 (shown in FIG. 2), is shown. Method 300 includes irradiating a silicon article, e.g. broadband radiation A (shown in FIG. 1). Irradiating the silicon article can include illuminating the silicon article with a halogen lamp, e.g., radiation source 118 (shown in FIG. 1), as shown in box 312. Irradiating the silicon article can include irradiating the silicon article with visible radiation, as shown with box 314. Irradiating the silicon article can include irradiating the silicon article with infrared radiation, as shown with box 316.

Method 300 also includes transmitting a portion of the radiation using the silicon wafer, as shown with box 320. The transmitted radiation can be filtered, as shown with box 330. Filtering can be done using a filter, e.g., filter 110, which excludes radiation outside of an predetermined narrowband, as shown with box 332. The narrowband can be centered at 1200 nanometers. The narrowband can extend between 1190 nanometers and 1210 nanometers. The narrowband can include radiation restricted to a wavelength of only 1200 nanometers.

Image data, e.g., image data D, is acquired from the transmitted radiation, as shown with box 340. The image data can be acquired from the filter radiation using an array responsive to infrared radiation, e.g., array 112 (shown in FIG. 1). An image of the silicon article, e.g., image E (shown in FIG. 4), is reconstructed from the image data as shown in box 350.

Using the reconstructed image of the silicon article, anomalies are identified in the reconstructed image, as shown box 360. The anomalies can include internal voids, as shown with box 362. The anomalies can include surface connected cracks, as shown with box 364. The anomalies can include internal cracks, as shown with box 366. It is contemplated that the image data used to reconstruct the image of the silicon article have information suitable for distinguishing internal voids from other types of anomalies, such as using edge detection or other image recognition techniques.

Figure 4A:
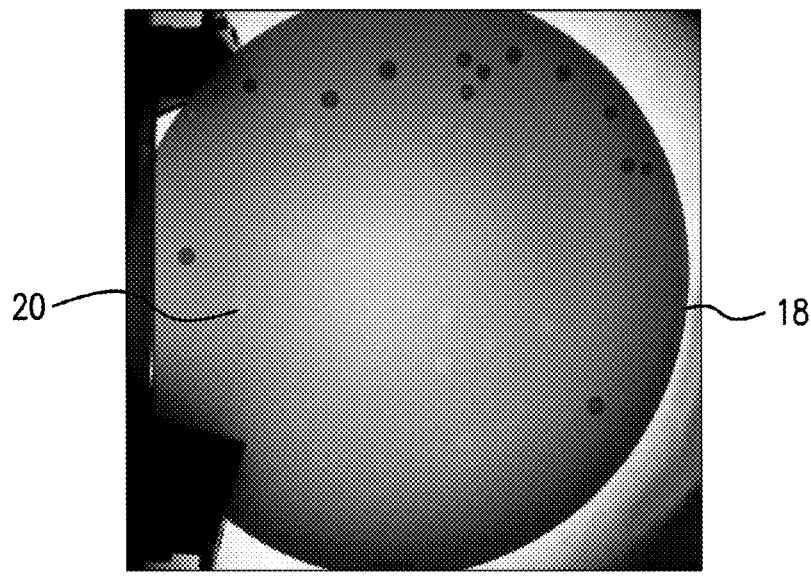
FIGS. 4A and 4B are images of a silicon wafer, showing anomalies within the wafer as indicated using image data acquired from an infrared imaging technique and a scanning atomic microscopy technique.
Figure 4B:
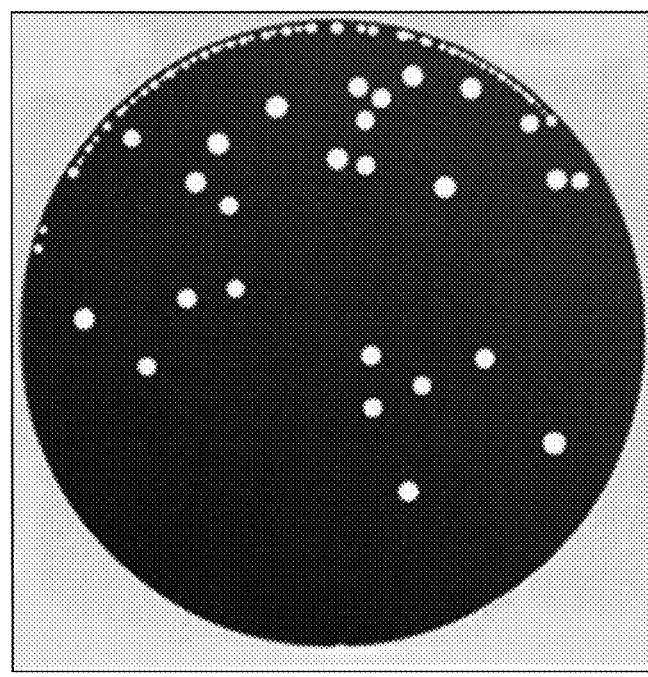

Referring to FIGS. 4A and 4B, exemplary images of a silicon wafer having internal voids, surface connected cracks, and internal cracks are shown. With respect to FIG. 4A, a wafer map image E constructed using image data received from silicon article inspection system 100 (shown in FIG. 1) is shown. Notably, each defect identified in the SAM data is discernable in the wafer map image E reconstructed using the image data received from silicon article inspection system 100. Moreover, anomalies indicated in the wafer image E have different contrasts, which allow for grouping the anomalies by defect type. In this respect the darker anomalies in wafer image E indicate locations of internal voids 18. Relatively light anomalies indicate locations of surface connected cracks 20. Intermediate darkness anomalies indicate locations of internal cracks 22.

With respect to FIG. 4B, a wafer image F reconstructed using SAM image data is shown. Notably, no information regarding the type of anomaly is discernable in FIG. 4B, which renders classifying based on void content and distribution in the wafer difficult more challenging compared to wafer image E.

The methods and systems of the present disclosure, as described above and shown in the drawings, provide for silicon article inspection apparatus, systems, and methods with superior properties including the capabilities to quickly identify internal voids within silicon wafers, layers, and bonds between silicon layers. While the apparatus and methods of the subject disclosure have been shown and described with reference to preferred embodiments, those skilled in the art will readily appreciate that changes and/or modifications may be made thereto without departing from the scope of the subject disclosure.

What is claimed is:
1. A method of inspecting a silicon article, comprising:
  irradiating a silicon article with infrared radiation,
    wherein the silicon article is a silicon wafer;

transmitting a portion of the infrared radiation through the silicon article;
filtering the infrared radiation transmitted through the silicon article;
acquiring image data from the filtered infrared radiation;
constructing an image of the silicon article using the image data acquired from the filtered infrared radiation; and
identifying one or more anomalies defined within the silicon article from the reconstructed image,
wherein filtering the infrared radiation includes filtering the infrared radiation to within a radiation narrowband extending between 1190 nanometers and 1210 nanometers,
wherein identifying one or more anomalies defined within the silicon article comprises identifying one or more of a void, a surface connected crack, and an internal crack defined within the silicon article.

2. The method of inspecting a silicon article as recited in claim 1, wherein the silicon article comprises a bond interconnecting a first silicon layer with a second silicon article.

3. The method of inspecting a silicon article as recited in claim 1, further comprising irradiating an entirety of a surface of the silicon article using a halogen lamp.

4. The method of inspecting a silicon article as recited in claim 1, further comprising irradiating the silicon wafer with broadband radiation.

5. The method inspecting a silicon article as recited in claim 4, wherein the broadband radiation comprises visible radiation.

6. The method of inspecting a silicon article as recited in claim 4, wherein the broadband radiation comprises infrared radiation.

7. The method of inspecting a silicon article as recited in claim 4, wherein the broadband radiation comprises a radiation narrowband centered at 1200 nanometers.

8. The method of inspecting a silicon article as recited in claim 1, wherein filtering the transmitted radiation comprises removing wavelengths outside of the radiation narrowband centered at 1200 nanometers.

9. The method of inspecting a silicon article as recited in claim 1, wherein acquiring image data comprises receiving the filtered radiation at a broadband sensor array.

10. The method of inspecting a silicon article as recited in claim 9, wherein acquiring image data comprises measuring the filtered radiation within a wavelength band extending between about 800 nanometers and about 1700 nanometers.

11. The method of inspecting a silicon article as recited in claim 1, wherein reconstructing an image of the silicon article includes reconstructing an image including a notch of a silicon wafer.

12. The method as recited in claim 1, further comprising distinguishing between a void, a surface connected crack, and an internal crack defined within the silicon article.

13. A silicon article inspection apparatus, comprising:
an illuminator arranged to illuminate a silicon article with broadband radiation;
a sensor array to generate image data from radiation emitted by the illuminator and transmitted by the silicon article; and
a filter disposed between the inspection location and the sensor array, the filter configured to allow narrowband radiation centered at about 1200 nanometers pass through the filter,
wherein the filter is opaque to incident radiation outside of a narrowband between 1190 nanometers and 1210 nanometers.

14. The silicon article inspection system as recited in claim 13, wherein the illuminator comprises a halogen lamp, and further comprising a manipulator arranged to insert and remove the silicon article from an inspection position defined between the illuminator and the sensor array.

15. The silicon article inspection system as recited in claim 13, the filter is configured to allow narrowband radiation including image data of one or more of a surface connected crack, an internal crack, and a void defined within a bulk silicon layer and a bond between a first silicon layer and a second silicon layer.

16. The silicon article inspection system as recited in claim 13, wherein the sensor array has high responsivity within a wavelength band extending between 900 nanometers and 1700 nanometers.

17. A silicon article inspection system, comprising:
a silicon article inspection apparatus as recited in claim 13;
a control module operatively connected to the silicon article inspection apparatus, wherein the control module is responsive to instructions recorded on a non-transitory machine-readable medium to:
irradiate a silicon article with infrared radiation;
transmit a portion of the infrared radiation through the silicon article;
filter the infrared radiation transmitted through the silicon article;
acquire image data from the filtered infrared radiation;
construct an image of the silicon article using the image data acquired from the filtered infrared radiation; and
identify one or more anomalies defined within the silicon article from the reconstructed image.

* * * * *